US00PP14895P2

(12) United States Plant Patent
Whetman

(10) Patent No.: US PP14,895 P2
(45) Date of Patent: Jun. 8, 2004

(54) DIANTHUS PLANT NAMED 'DEVON XERA'

(50) Latin Name: *Dianthus×hybrida*
Varietal Denomination: Devon Xera

(76) Inventor: John Whetman, Deer Park Farm, Chudleigh, Devon TQ13 ONH (GB)

( * ) Notice: Subject to any disclaimer, the term of this patent is extended or adjusted under 35 U.S.C. 154(b) by 0 days.

(21) Appl. No.: 10/676,190

(22) Filed: Sep. 30, 2003

(51) Int. Cl.[7] ..... A01H 5/00

(52) U.S. Cl. ..... Plt./272

(58) Field of Search ..... Plt./272, 278

*Primary Examiner*—Bruce R. Campell
*Assistant Examiner*—Annette H Para

(57) ABSTRACT

A new cultivar of Dianthus plant named 'Devon Xera' that is characterized by compound mounding habit, strong vigor, yellow-green foliage and crimson flowers that bloom from May to September. In combination these traits set 'Devon Xera' apart from all other existing varieties of Dianthus known to the inventor.

2 Drawing Sheets

Genus: Dianthus.
Species: ×*hybrida*.
Denomination: Devon Xera.

BACKGROUND OF THE INVENTION

The present invention relates to a new and distinct cultivar of carnation that is grown for use as an ornamental landscape and container plant. The new cultivar is known botanically as *Dianthus×hybrida* and will be referred to hereinafter by the cultivar name 'Devon Xera'.

'Devon Xera' is the product of a breeding program started by the inventor in 1980. The breeding program is not federally funded and is on going, conducted in a cultivated area of Houndspool, Dawlish, Devon, United Kingdom. The primary focus of the breeding program is to produce new cultivars of carnations that exhibit unique growth habit.

'Devon Xera' was selected in 2000 in Devon, United Kingdom from a large group of open pollinated seedlings. The criteria by which the inventor selected 'Devon Xera' was strong, saturated crimson flower color, long flowering season, large sized flowers, vigorous growth and compact habit.

'Devon Xera' is a hybrid plant that resulted from the open pollination of the female parent plant Dianthus 'Neon Star' (U.S. Plant Patent Allowed, Filed Feb. 7, 2002, application Ser. No. 10/071,058) and the male parent plant an unidentified cultivar of Dianthus. The closest comparison plant is Dianthus 'Fusilier' (unpatented) which exhibits small dull colored flowers and low vigor. 'Devon Xera' is distinguishable from 'Fusilier' by large, bright crimson flowers and strong vigor. 'Neon Star' exhibits purple flowers, prominently compact habit, short stems and grey-green leaves. 'Devon Xera' is distinguishable from 'Neon Star' by yellow-green foliage, crimson flowers, less compact habit, and longer stems.

Asexual reproduction of the new cultivar 'Devon Xera' was first accomplished by the inventor in 2000 in a cultivated area of Houndspool, United Kingdom. The method of asexual propagation used was stem cuttings. Since that time the characteristics of the new cultivar have been determined stable and are reproduced true to type in successive generations by vegetative propagation.

SUMMARY OF THE INVENTION

The following traits have been repeatedly observed and represent the characteristics of the new Dianthus cultivar 'Devon Xera'. These traits in combination distinguish this cultivar from all other commercial varieties known to the inventor. 'Devon Xera' has not been tested under all possible conditions and phenotypic differences may be observed with variations in environmental, climatic and cultural conditions without however any difference in genotype.

1. Dianthus 'Devon Xera' exhibits a compact mounding growth habit.
2. Dianthus 'Devon Xera' exhibits large crimson flowers.
3. Dianthus 'Devon Xera' exhibits vigorous growth.
4. Dianthus 'Devon Xera' exhibits yellow-green foliage.
5. Dianthus 'Devon Xera' is 15–20 cm. in height and 10–15 cm in width.
6. Dianthus 'Devon Xera' is an evergreen perennial herb.
7. Dianthus 'Devon Xera' blooms from May to September.
8. Dianthus 'Devon Xera' is hardy to minus 15° Centigrade.

BRIEF DESCRIPTION OF THE DRAWINGS

The accompanying color drawings illustrate the overall appearance of the new Dianthus variety 'DEVON XERA' showing colors as true as it is reasonably possible to obtain in colored reproductions of this type. Colors in the drawings may differ from the color values cited in the detailed botanical description, which accurately describe the actual colors of the new variety 'Devon Xera'.

The drawing on sheet 1 illustrates a 3-month-old plant in an 11 cm. container.

The drawing on sheet 2 is a close-up of a typical flower. The plants were grown from 3 cm-plugs in an open-sided polythene structure in Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Devon Xera'. Data was collected from plants grown in 1.5-liter containers grown under glass in Houndspool, United Kingdom. The color determinations are in accordance with the 2002 edition of The Royal Horticultural Society Colour Chart of The Royal Horticultural Society, London, England, except where general color terms of ordinary dictionary significance are used. No chemical were used to treat the plants. Growing conditions are typical to other Dianthus.

Botanical classification: Dianthus 'Devon Xera'.
Species: ×*hybrida*.
Common name: Devon dianthus.
Commercial classification: Hybrid.
Type: Perennial herb.
Use: Ornamental plant for small pots and containers.
Parentage: 'Devon Xera' is a hybrid plant that resulted from the open pollination of the following parent plants.
- *Female parent plant.*—Dianthus 'Neon Star'.
- *Male parent plant.*—Unidentified cultivar of Dianthus.

Plant description:
- *Bloom period.*—May to September.
- *Plant habit.*—Compact mounding habit.
- *Plant height.*—15–20 cm. in height.
- *Vigor.*—Strong vigorous growth.
- *Plant width.*—10–15 cm. in width.
- *Plant hardiness.*—Hardy to minus 15° Centigrade.
- *Type.*—Perennial evergreen herb.
- *Root system.*—Fibrous.
- *Sexually.*—Bisexual.
- *Propagation.*—Propagation is accomplished using stem cuttings.
- *Cultural requirements.*—Plant in full sun, well-drained and moderately fertile soil and keep well fertilized and watered.
- *Diseases and pests.*—Susceptible to known Dianthus pests and disease but no other susceptibilities to pests or disease are known to the inventor.
- *Time required to produce a rooted cutting.*—3 weeks are needed to develop roots on an initial cutting.
- *Temperature recommended for rooting.*—The air temperature needed is a minimum of 15° Centigrade air temperature and base heat of 21° Centigrade.
- *Crop time.*—4–6 months is needed to produce a finished 1.5-liter container size from a well-rooted cutting.

Stem:
- *Shape.*—Cylindrical.
- *Stem dimensions.*—15–20 cm. in length and 2 mm. in diameter.
- *Stem surface.*—Glabrous and glaucous.
- *Stem color.*—122A.
- *Branching.*—Numerous basal breaks.
- *Internode length.*—25–45 mm. between nodes.
- *Node dimensions.*—2 mm. in diameter and 3 mm. in length.
- *Node color.*—144C.

Foliage:
- *Type.*—Evergreen.
- *Shape.*—Lanceolate.
- *Division.*—Simple.
- *Apex.*—Acute.
- *Base.*—Decurrent.
- *Venation.*—Not prominent.
- *Margins.*—Entire.
- *Attachment.*—Sheathing.
- *Arrangement.*—Opposite and spiraling on stem.
- *Surfaces* (*adaxial and abaxial*).—Glaucous.
- *Leaf dimensions.*—40–50 mm. in length and 3–4 mm. in width.
- *Leaf color* (*adaxial surfaces*).—144C.
- *Leaf color* (*abaxial surfaces*).—144C.
- *Stipules.*—Absent.
- *Fragrance.*—Absent.

Flowers:
- *Inflorescence.*—Raceme.
- *Flower type.*—Single and symmetrical.
- *Flower shape.*—Salviform.
- *Flower dimensions* (*including calyx*).—25 mm. in length and 30 mm. in diameter.
- *Bud color.*—N138C.
- *Anthocyanin.*—Absent.
- *Bud dimensions.*—15–18 mm. in length and 7 mm. in width.
- *Bud shape.*—Cylindrical.
- *Petals.*—Persistent double petals, apopetalous, overlapping and sympetalous.
- *Petal number.*—5 petals in number.
- *Petal dimensions.*—30 mm. in length and 25 mm. in width.
- *Petal margin.*—Dentate (toothed 1–2 mm deep).
- *Petal shape.*—Obdeltoid.
- *Petal color* (*adaxial surface*).—Colors 53B, 53A, 145C and 53D are each individually present on each individual petal.
- *Petal color* (*abaxial surface*).—Colors 53B, 53A, 145C and 53D are each individually present on each individual petal.
- *Petal surfaces* (*adaxial and abaxial*).—Glabrous.
- *Calyx dimensions.*—7 mm. in width and 15 mm. in length.
- *Sepal color* (*adaxial surfaces*).—N138C.
- *Sepal color* (*abaxial surfaces*).—N138C.
- *Anthocyanin.*—Present.
- *Sepal number.*—5 in number.
- *Fused or unfused.*—Fused.
- *Epicalyx.*—4 bracts in number (2 larger and 2 smaller).
- *Bract dimensions* (*larger*).—4 mm. in diameter and 8 mm. in length.
- *Bract dimensions* (*smaller*).—3 mm. in diameter and 5 mm. in length.
- *Epicalyx dimensions.*—9 mm. in length and 4 mm. in diameter.
- *Epicalyx color* (*adaxial surfaces*).—138A.
- *Epicalyx color* (*abaxial surfaces*).—138A.
- *Anthocyanin.*—Present.
- *Peduncle dimensions.*—15–100 mm. in length and 1 mm. in diameter.
- *Peduncle color.*—N138C.
- *Fragrance.*—Slight fragrance.
- *Lastingness of flower.*—Each individual flower lasts 7 days at 20° Centigrade.
- *Stipules.*—2 in number.
- *Stipule dimensions.*—15 mm. in length and 3 mm. in width.
- *Stipule color.*—N138C.
- *Anthocyanin.*—Absent.

Reproductive organs:
- *Stamens.*—Number varies from 0–10 on individual flowers.

*Stamen color.*—53D.
*Stamen dimensions.*—15 mm. in length and 1 mm. in diameter.
*Anther.*—Number varies (with stamens) from 0–10 on individual flowers.
*Anther color.*—53D.
*Anther dimensions.*—2 mm. in length and 1 mm. in diameter.
*Attachment.*—Dorsifixed.
*Pollen.*—Present.
*Pollen color.*—53D.
*Styles.*—Two in number.
*Style color.*—53B.
*Style dimensions.*—15 mm. in length and 1 mm. in diameter.
*Stigma.*—Single stigma.
*Color of stigma.*—53B.
*Stigma height.*—5 mm. above petals at maturity.
*Ovary position.*—Superior.
*Ovary dimensions.*—6 mm. in length and 4 mm. in diameter.
*Ovary shape.*—Spindle shaped.
*Ovary color.*—Color ranges from 144B to 144C on the flowers of an individual plant.

Seed:
*Seed color.*—202A.
*Seed dimensions.*—2 mm. in length and 1 mm. in diameter.

I claim:

1. A new and distinct cultivar of Dianthus plant named 'Devon Xera' as described and illustrated herein.

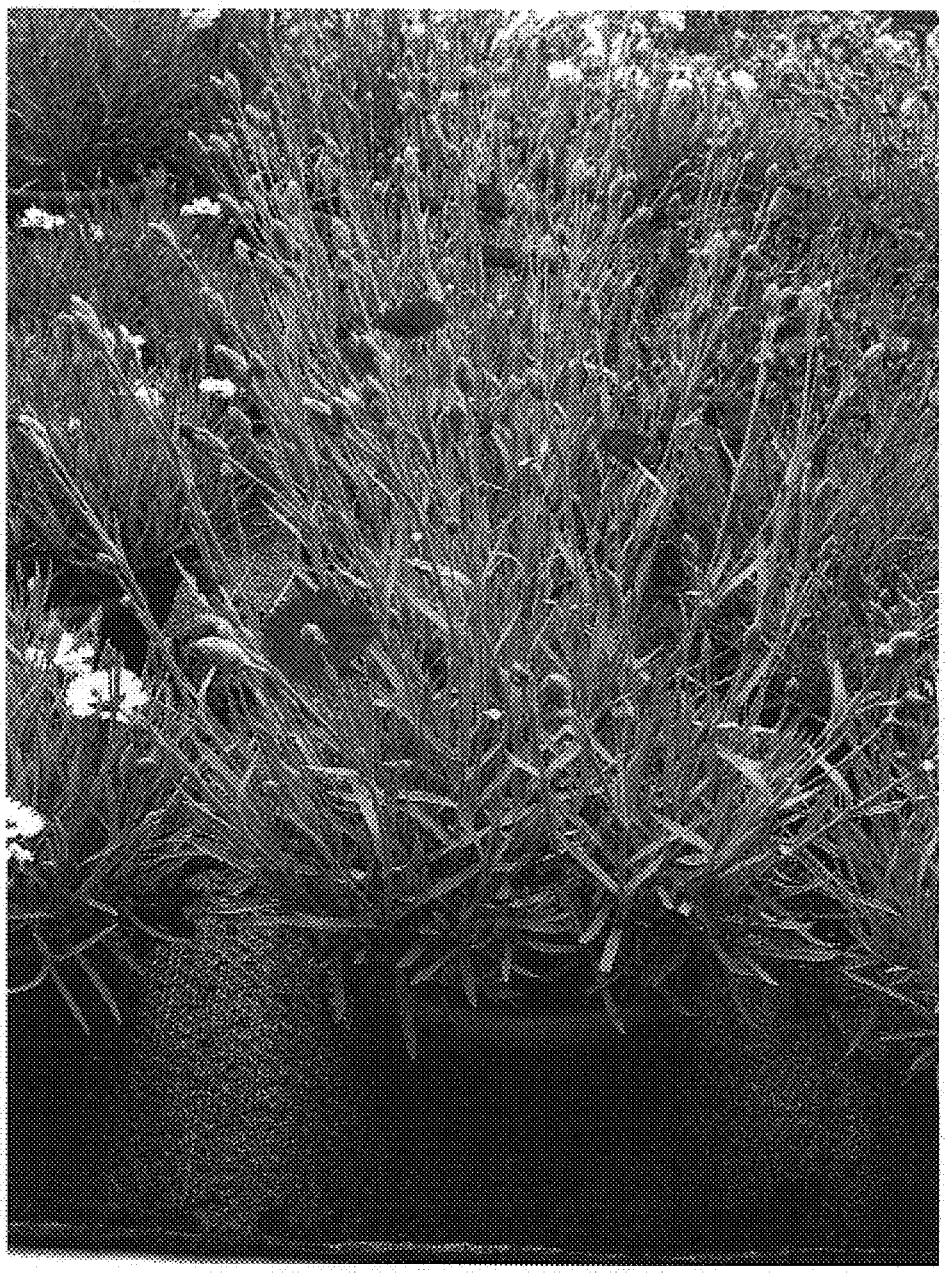

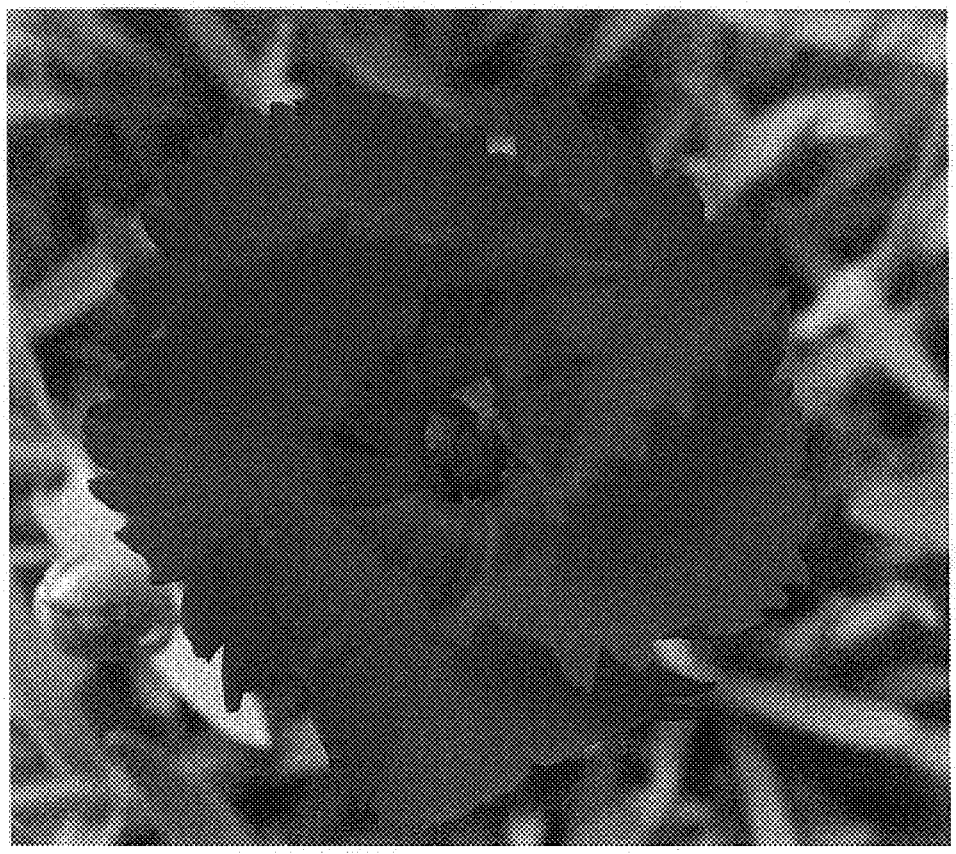

* * * * *